(12) United States Patent
Bailey et al.

(10) Patent No.: US 6,579,093 B2
(45) Date of Patent: Jun. 17, 2003

(54) HIGH SPEED TURBINE CARTRIDGE FOR USE WITH A MEDICAL/DENTAL HANDPIECE

(75) Inventors: Ronald L. Bailey, Harvester, MO (US); D. Keith Chipman, Ste. Genevieve, MO (US)

(73) Assignee: Young Dental Manufacturing Company 1, LLC, Earth City, MO (US)

( * ) Notice: Subject to any disclaimer, the term of this patent is extended or adjusted under 35 U.S.C. 154(b) by 0 days.

(21) Appl. No.: 09/877,979

(22) Filed: Jun. 8, 2001

(65) Prior Publication Data

US 2002/0119420 A1 Aug. 29, 2002

Related U.S. Application Data (60) Provisional application No. 60/271,050, filed on Feb. 23, 2001.

(51) Int. Cl.[7] .................................................. A61C 1/05
(52) U.S. Cl. ...................................... 433/132; 433/126
(58) Field of Search ................................ 433/126, 132, 433/82

(56) References Cited

U.S. PATENT DOCUMENTS

| | | | |
|---|---|---|---|
| 1,355,659 A | * 10/1920 | Evslin | 433/126 |
| 2,945,299 A | 7/1960 | Fritz | 433/126 |
| 3,815,241 A | 6/1974 | Lingenhohle et al. | 433/82 |
| 3,955,284 A | 5/1976 | Balson | 433/126 |
| 4,217,101 A | 8/1980 | Logé | 433/126 |
| 4,219,330 A | 8/1980 | Jaremus | 433/126 |
| 4,231,739 A | 11/1980 | Iudica | 433/126 |
| 4,318,695 A | 3/1982 | Lieb et al. | 433/132 |
| 4,348,180 A | * 9/1982 | Schuss | 433/126 |
| 4,406,470 A | 9/1983 | Kataoka et al. | 433/127 |
| RE31,965 E | 8/1985 | Kerfoot, Jr. | 433/132 |

(List continued on next page.)

OTHER PUBLICATIONS

Lares Research—1997 Catalog—pp. 1–16.

*Primary Examiner*—John J. Wilson
(74) *Attorney, Agent, or Firm*—Polster, Lieder, Woodruff & Lucchesi, L. C.

(57) ABSTRACT

A high-speed medical/dental handpiece includes a handle, which carries air, water, and light to a disposable cartridge which is received on the sleeve. The cartridge includes a head portion and a sleeve portion. The cartridge head defines a chamber having an upper and lower portions each of which receives a bobbin shaped sleeve bearing, and a central portion which receives a turbine. The bearings each form annular channels with their respective chambers. The cartridge includes water and air passages which direct water to the turbine so that the turbine is driven by an air/water mixture. Water is also directed to the upper bearing and grooves in the lower bearing chamber allow water to enter the annular channel around the lower bearing. Axial passages in the bearings enable water to pass from the annular chamber to the bit to contact the bit shaft. The air and water in the chamber are exhausted through the bit opening in the bottom of the head as well as through a plurality of exhaust ports in the head. The use of water in the turbine reduces the noise and vibration of the handpiece during operation of the handpiece and facilitates cooling of the bit. The cartridge sleeve includes a snap arm which engages the handle to hold the cartridge on the handle and a release arm which, when pressed, causes the snap arm to disengage the handle to allow for removal of the cartridge from the handle.

27 Claims, 5 Drawing Sheets

U.S. PATENT DOCUMENTS

| | | | |
|---|---|---|---|
| 4,533,324 A | 8/1985 | Nakanishi | 433/132 |
| 4,792,304 A * | 12/1988 | Schuss et al. | 433/126 |
| 4,795,343 A | 1/1989 | Choisser | 433/116 |
| 4,842,516 A | 6/1989 | Choisser | 433/132 |
| 4,869,779 A | 9/1989 | Acheson | 156/636 |
| 4,921,424 A | 5/1990 | Kimura | 433/114 |
| 4,941,828 A | 7/1990 | Kimura | 433/114 |
| 4,966,552 A | 10/1990 | Gonser | 433/132 |
| 5,088,924 A | 2/1992 | Woodward | 433/126 |
| 5,252,065 A | 10/1993 | Nakanishi | 433/126 |
| 5,252,067 A | 10/1993 | Kakimoto | 433/126 |
| 5,308,242 A | 5/1994 | McLaughlin et al. | 433/114 |
| 5,334,013 A | 8/1994 | Meller | 433/132 |
| 5,336,089 A | 8/1994 | Sakurai | 433/126 |
| 5,340,311 A | 8/1994 | Sakurai | 433/126 |
| 5,340,312 A | 8/1994 | Murase | 433/132 |
| 5,342,196 A | 8/1994 | Van Hale | 433/82 |
| 5,374,189 A | 12/1994 | Mendoza | 433/125 |
| 5,476,380 A | 12/1995 | Rosenstatter | 433/132 |
| 5,507,642 A | 4/1996 | Wohlgemuth | 433/132 |
| 5,538,425 A | 7/1996 | Reeves et al. | 433/126 |
| 5,554,026 A | 9/1996 | Van Hale | 433/82 |
| 5,772,435 A | 6/1998 | Dorman | 433/126 |
| 5,797,743 A | 8/1998 | Bailey | 433/126 |

\* cited by examiner

HIGH SPEED TURBINE CARTRIDGE FOR
USE WITH A MEDICAL/DENTAL
HANDPIECE

CROSS-REFERENCE TO RELATED APPLICATIONS

This application claims priority to Provisional Application Ser. No. 60/271,050, entitled "High Speed Turbine Cartridge For Use With A Medical/Dental Handpiece", filed Feb. 23, 2001, and which is incorporated herein by reference.

BACKGROUND OF THE APPLICATION

This invention relates to medical/dental handpieces, and in particular to a disposable air-driven turbine cartridge designed for use in high-speed handpieces.

Dentists use high speed turbines in dental handpieces to rotate dental burrs at high speeds (i.e., in excess of 100,000 rpm). Surgeons use analogous handpieces when drilling or operating on bone. To enable the drill to be rotated at such high speeds, the drill bit is held by bearings and a turbine in the head of the handpiece. Air is forced into the head of the handpiece to rotate the turbine, which in turn rotates the drill bit. The air is then exhausted out the back of the handpiece. Generally the bit or bur is retained in a bur tube, and the bur tube is piloted through the turbine and the A bearings. When the bur is retained in the bur tube, the bur tube defines the axis of rotation of the turbine and the bur. For the bur to rotate about its own axis, the axis of the bur must be perfectly aligned with the axis of the bur tube. This alignment can be difficult to precisely obtain. When the axes of the bur and bur tube are not precisely aligned, the bur can wobble as it is rotated. This wobble can then make it difficult to carry out precise procedures.

When the handpiece is used, the head of the handpiece, which is inserted in the patient's mouth, becomes contaminated. The handpiece must thus be cleaned and sterilized between uses. The most effective way to fully sterilize the hand piece is to autoclave it. However, the heat from the autoclave can, over time, damage the turbine bearings. Once the bearings have been damaged, the high speed handpiece cannot run effectively at the necessary speeds to be used as a drill. Further, grit or particulate matter can get into the handpiece. This grit can sometimes be removed by ultrasonically cleaning the handpiece. However, ultrasonic cleaning can also damage the bearings. Proper cleaning and sterilizing of the handpiece will thus effectively shorten the life of the high speed handpiece.

High speed handpieces are very expensive. To prevent the possibility of shortening the useful life of the handpiece, some dentists resort to merely wiping down the outside of the handpiece. This may clean off the contaminants on the outside of the handpiece, but it cannot not properly disinfect the exterior of the handpiece. Further, merely wiping down the outside of the handpiece does not clean or disinfect the interior of the handpiece. Grit which may accumulate in the handpiece will therefore remain in the handpiece unless the handpiece is opened and manually cleaned.

To overcome this problem, some manufacturers have introduced fully disposable high speed handpieces. One such handpiece, produced by OralSafe, of Temecula, Calif., is shown in U.S. Pat. No. 5,308,242, to McLaughlin et al. Another is shown in U.S. Pat. No. 4,842,516, to Choisser. Although fully disposable handpieces overcome the problems associated with the inability to fully clean a high speed handpiece without ruining its bearings, they are still expensive.

Currently available high speed handpieces typically include a fiber-optic cable to light the area where the doctor is working in the patient's mouth and a water stream to cool the bit as the dentist performs a drilling operation on the patient's teeth. Typically, the water and light outputs are located on the sleeve of the handpiece, behind the head which carries the turbine. The placement of the light and water outputs can be seen, for example, in U.S. Pat. No. 4,966,552 to Gonser. The light comes from an area behind the head of the handpiece and does not adequately light the work area in the patient's mouth. Because the light is rather far from the drill bit, the light becomes diffused due of the longer distance traveled, and thus does a poorer job of lighting the workarea. Further, because the light comes from one direction, rather than all around the drill, it is possible that the light will be totally ineffective for use when the handpiece is used in certain angles. Similarly, with the water exiting the handpiece from the sleeve, the water is not accurately aimed at the drill bit, or may not contact the drill bit. Thus, the drill bit may not be adequately cooled during use.

High speed handpieces employ an air driven turbine to rotate the bit. Because of the high speeds at which the bit is rotated, the bit, the turbine, and the bearings in the handpiece head can become quite hot, making the handpiece uncomfortable for the dentist to hold and for the patient to have in his mouth. Although the air which drives the turbine does remove some of the heat as the air is exhausted from the unit, it would be desirable to be able to cool the head of the handpiece even further, to make the unit more comfortable for the patient to have in his mouth and for the dentist to hold.

High speed handpieces emit a high frequency sound during use of the handpiece. Studies have found that dentists who frequently use high speed handpieces show a loss of hearing at these frequencies. The sound is also typically considered to be a grating sound. It would thus be desirable to produce a handpiece which emits a sound having a lower frequency. Such a lower frequency sound would not be as bothersome to patients and dentists. Bailey, U.S. Pat. No. 5,797,743, which is incorporated herein by reference, and which is assigned to the same assignee as the current invention, discloses a disposable cartridge for use with high-speed handpieces. The cartridge disclosed in that patent works very well and solves the above noted problems. However, it does not solve the problem associated with the high frequency sound output by currently available handpieces. The medical and dental industries have long been trying to make a high-speed handpiece that will run quietly. We know of no high-speed handpiece that runs quietly or which does not produce a high pitched squeal during operation.

SUMMARY OF THE INVENTION

Briefly stated, a high-speed medical/dental handpiece removably receives a bur and is operable to drive the bur at speeds in excess of 100,000 rpm and upwards of 300,000 rpm, or faster. The handpiece includes a sleeve which carries air, water, and light to a head at an end of the sleeve. The head defines a chamber having an upper portion, a central portion, and a lower portion. The chamber lower portion has an opening therein through which the bit can pass. The chamber upper and lower portions each house a bearing and the chamber central portion houses a turbine which is positioned between, but not journaled in, the bearings. The bearings are preferably made of a low temperature plastic, such as a polycarbonate, an acetal copolymer, or an acrylate.

The camber upper portion is countersunk to receive a ball bearing, against which the bit presses during operation of the handpiece. Thus, the ball bearing comprises a thrust bearing for the bit. The head includes air and water passages which direct both air and water to the turbine so that the turbine is driven by an air/water mixture.

Water is additionally passed into the upper and lower bearing chambers and is brought into intimate contact with the bit within the housing to facilitate cooling of the bit. The bearings are bobbin shaped, and, with the bearing chambers, define an upper and lower annular channels. Although the water input line could be in direct communication with both the upper and lower bearing chambers, in the disclosed embodiment, the water line is in direct communication with only the upper bearing chamber. Axial slots around the lower bearing chamber allow water to enter the lower bearing chamber from the central, or turbine, chamber. Thus, during operation of the handpiece, water is dispersed throughout the complete chamber. Preferably, the upper and lower bearings each have an axial bore which places the annular chamber in communication with the bit shaft, so that water which enters the annular channels will flow through the bearing passages to contact the bit. Additionally, water is drawn into the interface between the bearings and the turbine. The chamber is provided with a plurality of exhaust ports on a lower surface of the chamber through which the air/water mixture in the head is exhausted. Thus, a separate exhaust line which extends through the handpiece is not required. The size and number of exhaust ports reduces the velocity of the exhausted air/water mixture.

The handpiece head is preferably a disposable cartridge which is received on an autoclavable sleeve. The cartridge includes a body removably mountable to the sleeve and a cap mounted to the body. The body and cap cooperate to define the chamber. The cartridge body includes a hollow sleeve portion and a head portion. The cartridge body sleeve portion is slidably mounted over an end of the handpiece sleeve. The cartridge body sleeve includes a snap arm having an inwardly directed finger at a free end thereof which engages the handpiece sleeve to hold the cartridge on the sleeve. The cartridge sleeve also includes a release arm operatively connected to the snap arm by a fulcrum; whereby, the snap arm finger is brought out of engagement with the handle by pressing down on the release arm.

The cap includes a heel (or back portion) which, when the cartridge is placed on a handle or sleeve, abuts a light tube. The cap includes a lens beneath the heel which directs light from the light tube toward the bit. At least the cap heel and lens are translucent or transparent to allow light to pass into the cap and through the lens. The cap also includes a reflective surface in the heel which directs light from the light tube into the lens.

DESCRIPTION OF THE PREFERRED EMBODIMENT

Figures 1, 2, 3:
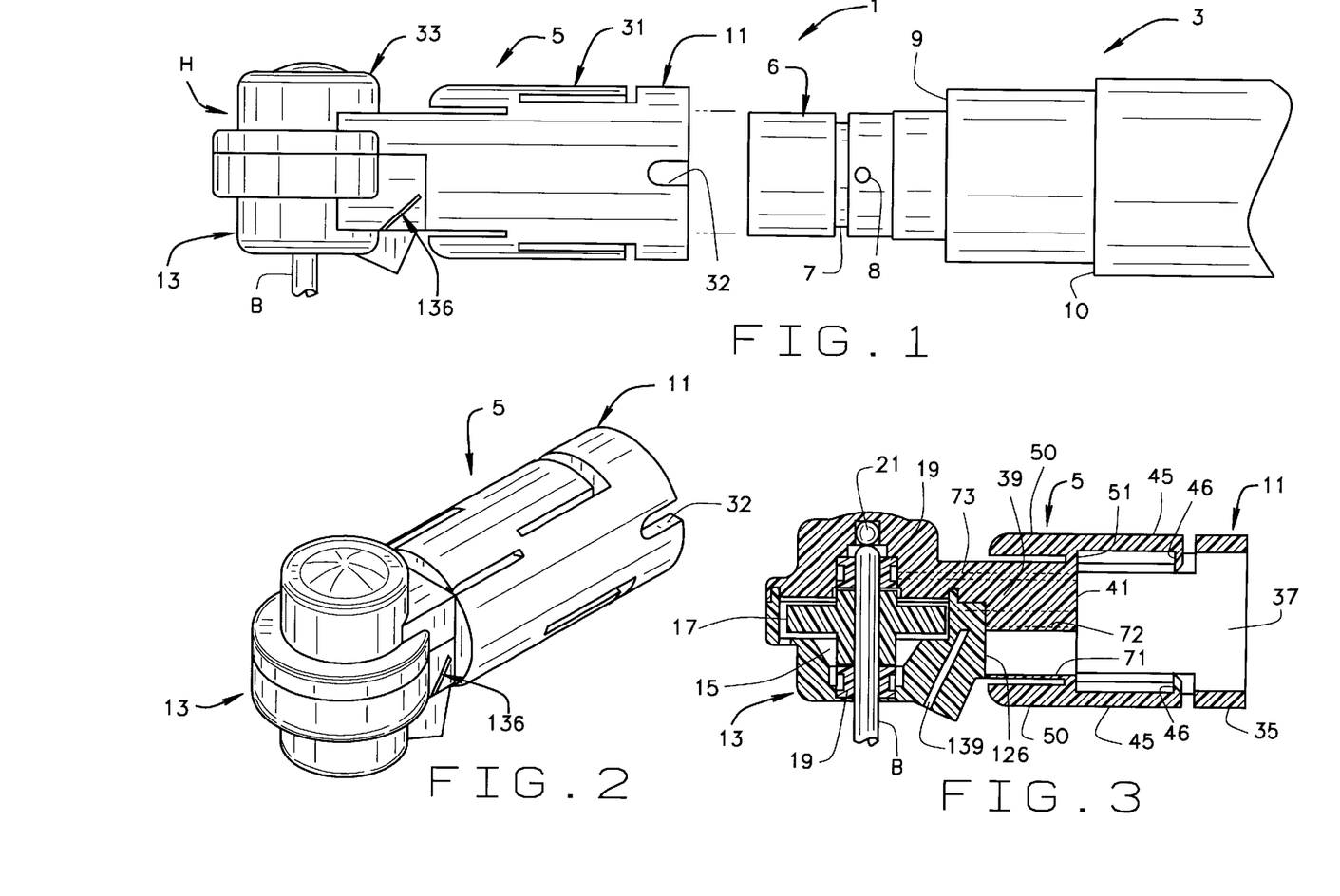
FIG. 1 is an exploded side elevational view of a handpiece of the present invention, including a disposable cartridge and an autoclavable sleeve upon which the cartridge is removably mountable.
FIG. 2 is a perspective view of the cartridge.
FIG. 3 is a cross-sectional view of the cartridge.
Figure 4:
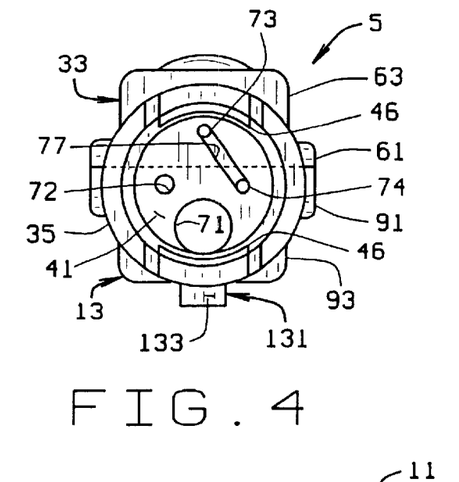
FIG. 4 is a rear elevational view of the cartridge.
Figure 5:
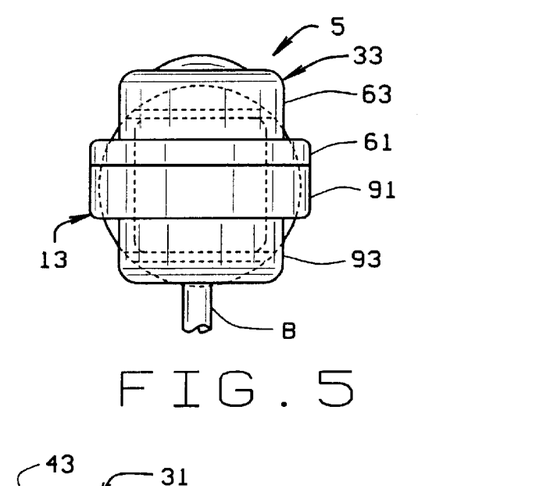
FIG. 5 is a front elevational view of the cartridge.
Figure 6:
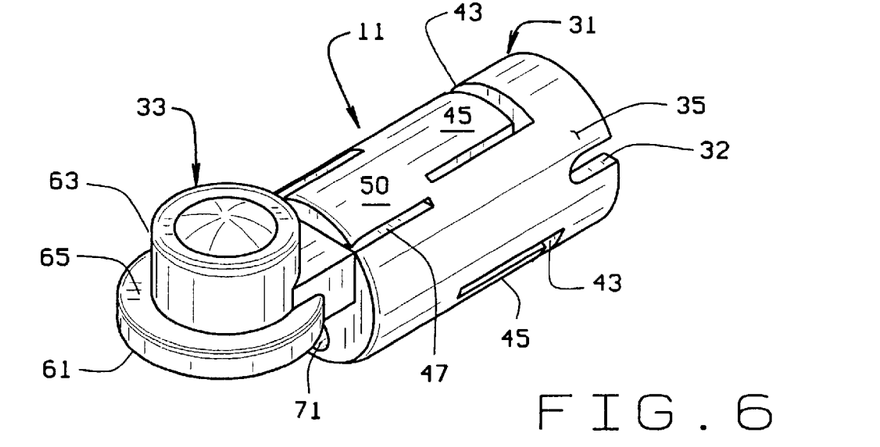
FIG. 6 is a perspective view of a body of the cartridge.

A high-speed handpiece 1 is shown generally in FIG. 1. The handpiece 1 includes of a hollow, open-ended handle or sleeve 3 which removably receives a disposable cartridge 5. A connector at the back of the sleeve 3 connects the handpiece handle to a supply hose which is connected to sources of air, water, and light to deliver air, water, and light to the handpiece. The connector can be a standard Midwest-type connector. Preferably, however, it is a connector as shown in co-pending application Ser. No. 60/272,513, entitled Swivel Connector For Dental And Medical Handpieces, filed on the Feb. 23, 2001, and which is incorporated herein by reference. The cartridge 5 is received at the front of the handpiece sleeve to define the head of the handpiece.

The sleeve or handle 3 carries an air line, a water line, and a light tube (i.e., a bundle of fiber optics). The sleeve can also include an exhaust tube, however, an exhaust tube is not required by the present cartridge, as will become apparent below. The air and water line terminate at the forward end of the sleeve or handle 3; the light tube extends a slight bit beyond the end of the handle 3, as discussed below. The handle 3 includes a nose 6 having a circumferential groove 7 and a pin 8. The groove 7 is spaced rearwardly of the front of the nose 6, and the pin 8 is spaced behind the groove 7. A first shoulder 9 is spaced slightly behind the pin 8, and a second shoulder 10 is spaced behind the first shoulder 9. Thus, the forward end of the sleeve 3 includes two shoulders or steps which increase the outer diameter of the sleeve 3. The remainder of the sleeve is preferably substantially constant in diameter. The sleeve can either be a straight sleeve, or can be bent to form a contra angle.

The cartridge 5 is shown generally in FIGS. 2–5. It includes a cartridge body 11 and a cartridge cap 13. The body 11 and cap 13 snap together to form a head H of the handpiece having an internal chamber 15. The chamber 15 has an upper portion, a central portion, and a lower portion. An opening 111 is formed in the chamber lower portion through which a bit B can pass. The chamber central portion houses a turbine 17. The chamber upper portion and lower portions house an upper and lower bearings 19. The turbine 17 is positioned between the upper and lower bearings. The bit B, such as a dental bur, is journaled through the bearings and turbine to be rotationally driven by rotation of the turbine in the chamber 15. A ball bearing 21 in the cartridge body 11 above the upper bearing 19 operates as a thrust bearing for the bit B.

The cartridge body 11 is shown in more detail in FIGS. 6–12. The cartridge body 11 includes a sleeve portion 31 and a head portion 33. A slot 32 extends inwardly from the back edge of the body sleeve 31. The head portion 33 is separated from the sleeve portion 31 by a neck 34. The sleeve portion 31 has a generally cylindrical wall 35 defining a generally cylindrical chamber 37 (FIG. 3). A thick wall 39 extends from the front of the wall 35 and forms a forward surface 41 of the chamber 37. As described below, the wall 39 forms a manifold. A pair of opposed generally U-shaped slots 43 are formed in the wall 35 and extend rearwardly from the chamber forward surface 41. The slots 43 define upper and lower squeeze arms 45 which extend rearwardly from the chamber forward surface 41. The arms 45 each have inwardly directed fingers 46. (FIG. 3). When the cartridge 5 is slid onto the handpiece handle 3, the fingers 46 are received in the handpiece groove 7. To properly orient the cartridge 5 with respect to the handle 3, the slot 32 slides about the pin 8.

Figure 7:
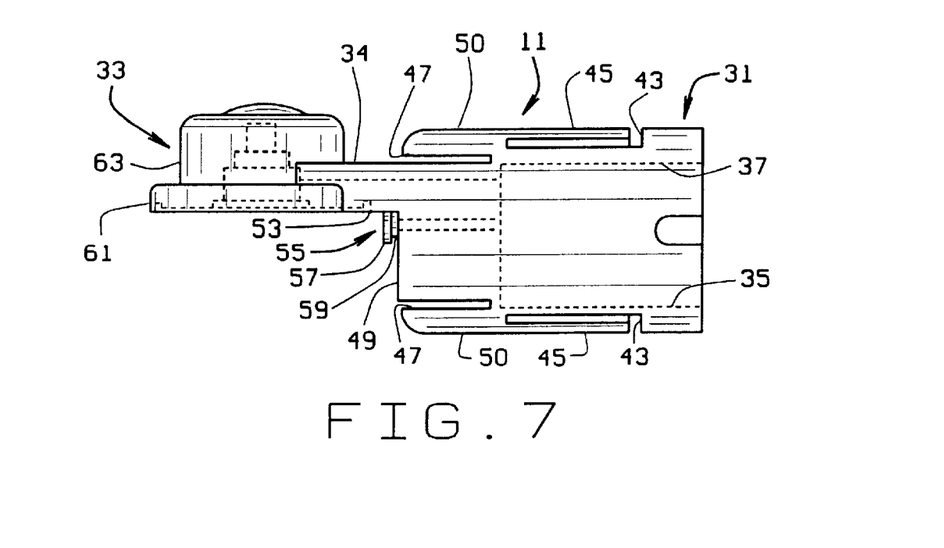
FIG. 7 is a side elevational view of the cartridge body.
Figure 8:
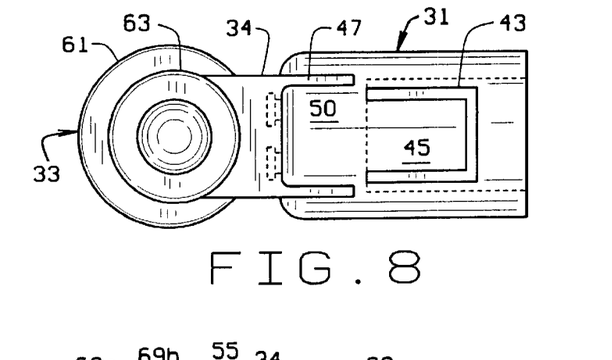
FIG. 8 is a top plan view of the cartridge body.
Figures 9, 10, 11:
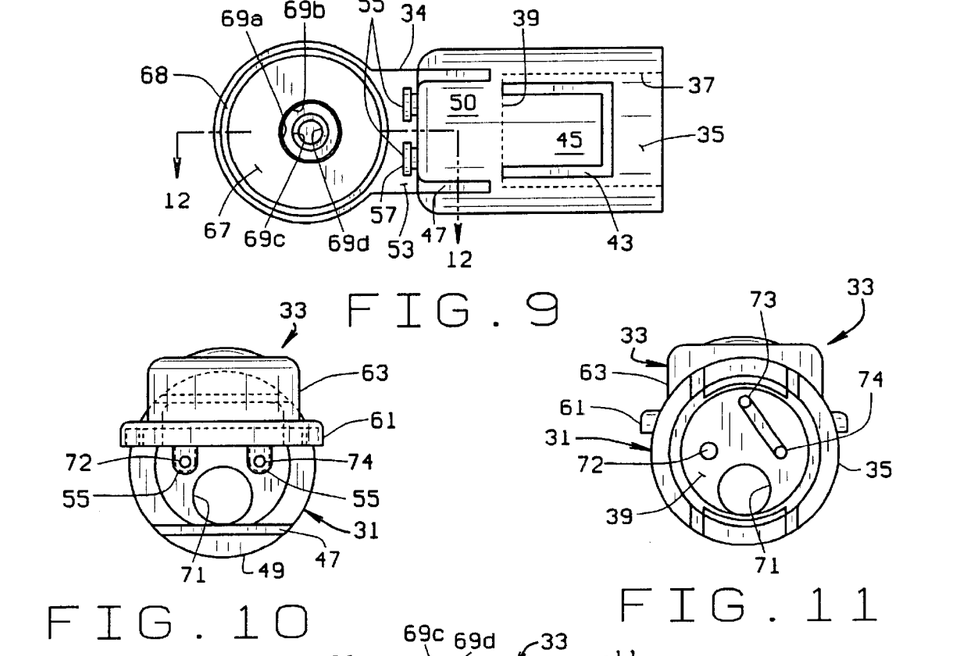
FIG. 9 is a bottom plan view of the cartridge body.
FIG. 10 is a front elevational view of the cartridge body.
FIG. 11 is a rear elevational view of the cartridge body.
Figure 12:
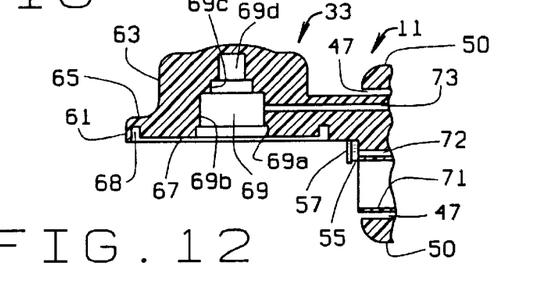
FIG. 12 is a fragmentary cross-sectional view of the cartridge body taken along line 12—12 of FIG. 9.
Figure 13:
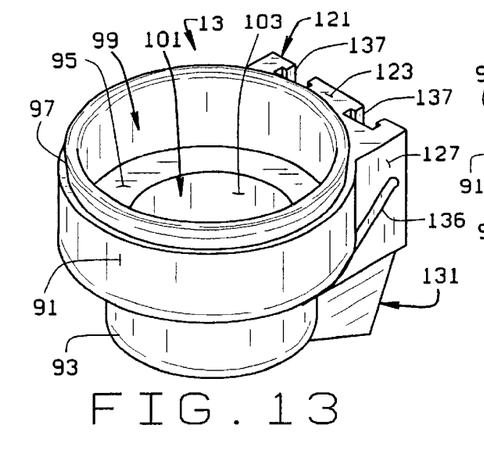
FIG. 13 is a perspective view of a cap of the cartridge.

Upper and lower slots 47 extend rearwardly from the front surface 49 of the wall 39 to form forward squeeze arms 50. The slots 47 are co-planar with the slots 43, and are spaced slightly radially inwardly from the slots 43, such that the bottom surface of the arms 50 are slightly inward of the bottom surfaces of the arms 45. The arms 50 are effectively a continuation of the arms 45 as best seen in FIG. 7. The arms 50 and 45 are separated by a fulcrum 51. The fulcrum 51 is defined by the back of the slots 47 and the periphery of the chamber forward surface 41. When the arms 50 are squeezed, the free end of the arms 45 are urged radially outwardly relative to the wall 35. The arms 45 and 50, the fulcrum 51, and the fingers 46 are sized such that when the arms 50 are squeezed, the fingers 46 will be withdrawn from the handle groove 7, and the cartridge can be removed from the handle 3. To accomplish this, the cartridge body neck 31 and the handle nose 6 are sized so that the arms 50 are spaced forwardly of the end of the nose 6 when the cartridge 5 is placed on the handle 3.

The cartridge body neck 34 has a generally flat bottom surface 53. A pair of spaced apart projections 55 are formed at the intersection of the forward surface 49 of the wall 39 and the neck bottom surface 53. The projections 55 are preferably generally U-shaped. A front face 57 covers each projection 55. The faces 57 are similarly shaped to the projections 55, but are larger than the projections 55. Thus, the faces 57 form shoulders 59 which surround the projections 55.

The cartridge body head portion 33 has the general configuration of a brimmed hat. It has a bottom section 61 which extends from the neck 34. The bottom section 61 is essentially circular in plan, except for where it intersects the neck 34. A cylindrical portion 63 rises up from the top of the bottom section 61. The cylindrical portion 63 is smaller in diameter than the bottom section 61 and is generally centered with respect to the bottom section 61. Thus, a shoulder or lip 65 is formed by the bottom section 61 and cylindrical portion 63.

The bottom surface 67 of the head 33 is generally flat. As can be appreciated, the head bottom surface 67 forms an upper surface of the chamber 15. A circular groove 68 (FIGS. 9 and 12) is set slightly inwardly from the periphery of the bottom section 61 on the head bottom surface 67. A stepped chamber 69 is formed in the center of the head 33 and opens onto the head bottom surface 67. The chamber 69 has four sections, 69a–d. The four sections are concentric and of differing heights, as will be explained below. Chamber 69d receives the ball bearing 21. The bit extends into chamber 69c. Chamber 69b receives one of the bearings 19. Chamber 69a receives a top portion of the turbine 17. As seen in FIG. 3, the chamber 69c has a diameter greater than the bit B, and the bit B bears against the ball bearing 21. Thus, during operation the ball bearing will operate as a thrust bearing.

Four channels 71–74 (FIG. 11) extend through the manifold 39 to pass light, water, and air from the handpiece handle 3 to desired areas. Channel 71 is the largest, and is sized to receive the light tube from the handle 3. The light tube, for example, can be a bundle of optic fibers. The channel 71 is at the bottom of the wall 39, such that the light tube can pass light directly to the cartridge cap 13, as is discussed below. The channel 72 delivers air to the cartridge chamber 15 to drive the turbine. The channel 73 extends through the neck and head cylindrical portion to deliver water to chamber section 69b to cool the bearings during operation of the handpiece 1. Lastly, the channel 74 mates with a channel in the head cap 13, as described below, to deliver cooling water to the bit B. The channels 73 and 74 are connected by a small slot 77 to facilitate entry of water into each of the channels.

The cartridge cap 13 is shown in detail in FIGS. 13–18. The cap has an upper generally circular wall 91 and a lower generally circular wall 93. The lower wall 93 has a circumference and diameter smaller than that of the upper wall 91. Hence, there is a floor or shoulder 95 extending from the lower wall to the upper wall. A circular rib 97 extends upwardly from the top surface of the wall 91. The rib 97 is sized and shaped to be snappingly received in the cartridge body head groove 68. The interaction of the cap rib 97 with the body groove 68 help hold the cartridge together during use.

The upper wall 91 and floor 95 define a chamber 99. The lower wall 93 defines a chamber 101 concentric with, but smaller in diameter than, the chamber 99. The chamber 101 has sloping side walls 103 giving it the shape of a truncated cone. A bearing chamber 105 extends from the bottom of the wall 103 of the chamber 101. The bearing chamber 105 has a generally cylindrical side wall 107 and a floor 109. An opening 111 is formed in the center of the floor 109 through which the bit B passes. A series of vertically or axially extending, spaced-apart grooves 113 are formed in the bearing chamber wall 107. Preferably, the grooves 113 are formed all the way around the bearing chamber wall 107. The grooves are vertical grooves, and extend down from the top of the wall 107 approximately ½ the height of the wall. As will be described below, the grooves 113 allow for water to accumulate around the bearing 19 to cool the bearing 19 and the bit B. A series of openings 115 are formed in the floor 95 at the forward end of the cap 13. The openings 115 do not extend all around the wall 95. Rather, they extend over an arc of about 140°–145°. Preferably, the openings are not symmetrical about a center line of the cap which runs from the front of the cap. Rather, holes to one side of the center line define an arc of about 90° and holes on the other side of the centerline define an arc of about 50°–55°. The holes 115, as will be explained below, allow for operating air and water to be exhausted from the cartridge.

A heel 121 extends from the back of the cap 13. Thus, the walls 91 and 93 do not form complete circles. The heel has a top surface 123, a back surface 125, side surfaces 127, and a bottom surface 129. The heel 121 extends from the top of the cap upper wall 91 to about midway down the cap bottom wall 93, such that the heel bottom 129 is about even with the bottom of the cap chamber 101 or the top of the cap bearing chamber 105. A lens 131 is formed at the bottom of the heel 121 and has a sloped back surface 133 and a forwardly sloped bottom surface 135. The lens front and back surfaces 133 and 135 intersect at an angle of about 90°. The lens bottom surface 135 begins at a point beneath the bottom surface of the cap, and slopes upwardly to intersect the cap bottom surface beneath the sloped wall 103 of chamber 101. The lens 131 is narrower than the heel.

Figure 14:
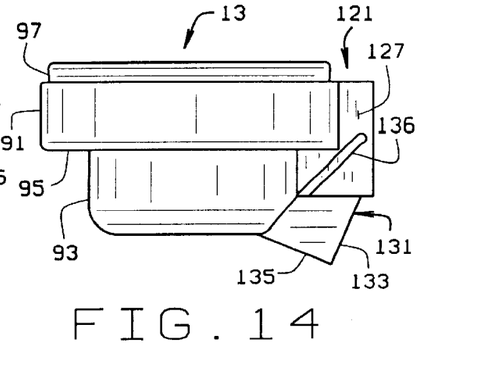
FIG. 14 is a side elevational view of the cartridge cap.

A reflective surface 136 is formed in the heel 121 above the lens 131. The reflective surface 136, which can be formed as a slit in the side wall 127 of the heel, extends diagonally from the forward, bottom corner of the heel, as seen in FIG. 14, upwardly towards the rear wall 125. The surface 136 does not reach all the way to the heel rear wall 125. The reflective surface 136 defines an angle with the heel rear wall 125 to direct light which enters the heel 121 through the rear wall 125 downwardly into the lens 131. Preferably, the reflective surface defines an angle of about 45° with the rear wall. When the cartridge 5 is placed on the handle 3, the light tube in the handle extends into the channel 71 of the cartridge body 11 so that the light tube substantially abuts the rear surface 125 of the cartridge cap 13. Thus, light which is passed through the light tube is directed into the cap 13 through the heel rear surface 125. The light which impinges upon the reflective surface 126 will be directed into the lens, so that light will be focused around the bit B, thereby illuminating the work area in patient. To accommodate the transfer of light through the cartridge cap 13, at least the heel 121 and lens 131 are made from light transmitting material. Preferably, the whole cap 13 is made from light transmitting material. For example, a translucent or transparent lens quality polycarbonate can be used to make at least the heel 121 and lens 131, if not the whole cap 13.

Figure 15:
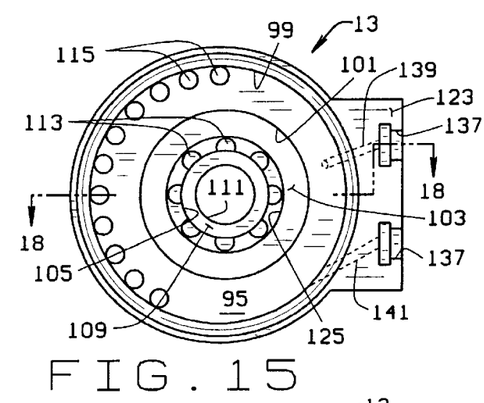
FIG. 15 is a top plan view of the cartridge cap.
Figure 16:
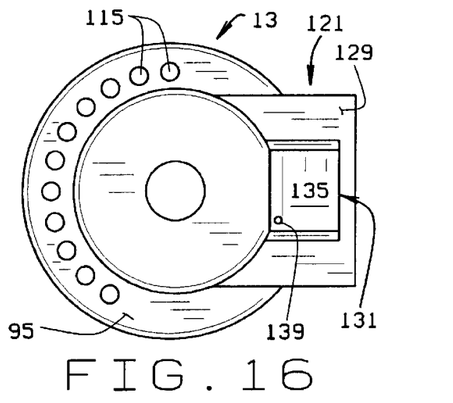
FIG. 16 is a bottom plan view of the cartridge cap.
Figure 17:
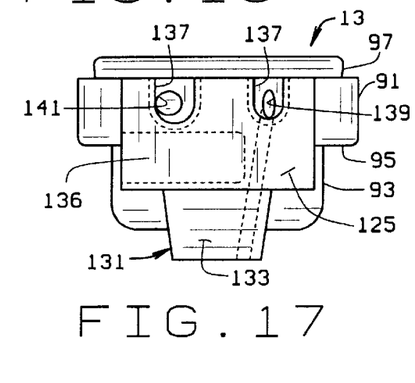
FIG. 17 is a rear elevational view of the cartridge cap.
Figure 18:
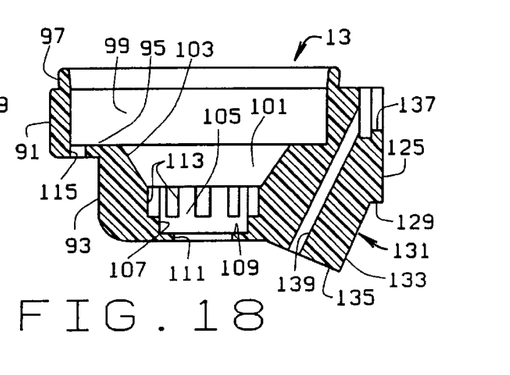
FIG. 18 is a cross-sectional view of a cap of the cartridge taken along line 18—18 of FIG. 15.

A pair of generally U-shaped grooves 137 (FIGS. 17–18) are formed in the heel back surface 125 and depend from the heel top surface 123. The grooves have a larger forward portion giving them a generally T-shaped appearance from above, as seen in FIG. 15. The grooves 137 are sized and shaped to receive the projections 55 of the cartridge body 31. A channel 139 extends from one of the grooves 137 to the bottom surface 135 of the lens 131. The channel 139 preferably exits the lens near where the lens bottom surface 135 intersects the bottom of the cap, as seen in FIG. 16. The channel 139 is angled so that the water exiting the channel will be sprayed directly at the bit. A second channel 141 (FIG. 15) extends from the other groove 137 and exits into the chamber 99. When the cartridge cap 33 is assembled to the cartridge body 31, the channel 139 is in fluid communication with the body channel 74 to deliver water to the bit, to directly cool the during use of the cartridge. The cap channel 141 is placed in fluid communication with the body channel 72 to deliver operating air to the chamber 99. The channel 141 is angled relative to the channel 72 so that the air will not enter the chamber along a diameter of the chamber. Rather, the air enters the chamber on a diagonal, so that the air can optimally drive the turbine.

Figure 19:
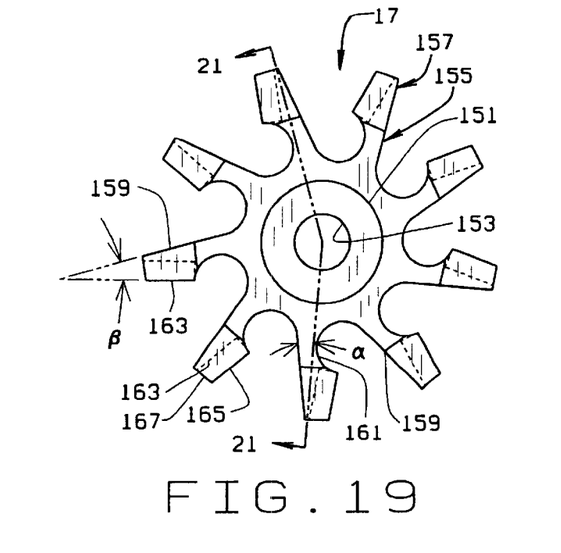
FIG. 19 is a top plan view of a turbine used in the cartridge.
Figure 20:
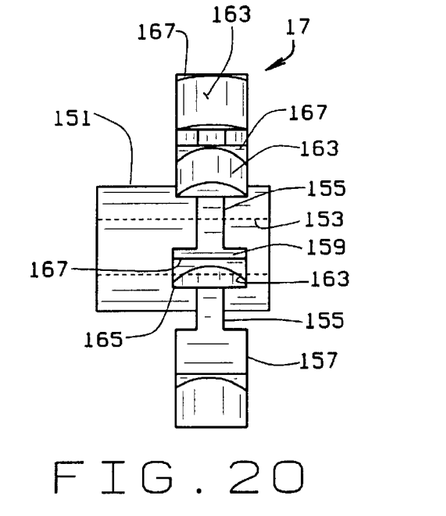
FIG. 20 is a side elevational view of the turbine.
Figure 21:
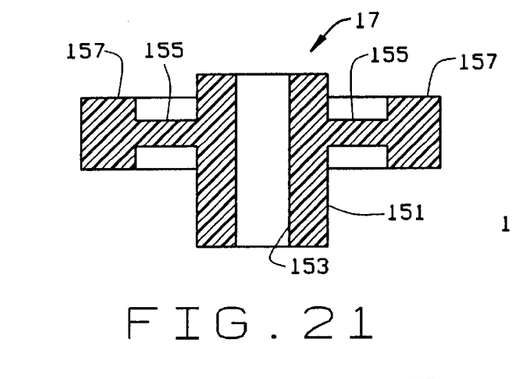
FIG. 21 is a cross-sectional view of the turbine taken along line 21—21 of FIG. 19.

Although a standard turbine will suffice, the turbine 17 shown in FIGS. 19–21 is preferred. Preferably, the turbine is a plastic turbine. Preferably, it is made from Nylatron®, an internally lubricated, tough, strong, resilient and highly wear resistant cast resin made of nylon compounded with molybdenum disulfide and available from DSM Engineering Plastic Products, Inc. of Evansville, Ind. The turbine 17 includes a generally cylindrical turbine body or stem 151 with a passage 153 extending from the top to the bottom of the body 151. The passage 153 is preferably about 0.06" in diameter to admit the shaft of the bit B through the turbine body 151. This size creates a friction fit with the bit shaft, so that the bit will rotate with the turbine, as the turbine is rotated. The turbine body has a diameter slightly smaller than the diameter of the body chamber 69a and a length sufficient to reach from the top of the body chamber 69a to the bottom of the cap chamber 101. A plurality of arms 155 extend from the turbine body 151 which have turbine blades 157 at their ends. The arms 155 and blades 157 have colinear leading edges or surfaces 159. The leading edges do not extend radially from the body. Rather, they form an angle α of about 10° with a radius of the body 151. The trailing surfaces 161 of the arms define a segment of a circle. The segment is about 165°–170°. The leading surfaces 159 extend from the end of the trailing surface, to form a generally J-shaped edge, as seen in FIG. 19. The trailing surface 163 of the blade 157 is curved. The outer edge 165 of the blade trailing surface 163, if continued inwardly, would intersect the center of the circle defined by the trailing surface 161 of the turbine arm 155. The outer edge 165 of the blade's trailing surface 163 defines an angle β of about 15°–20° with the arms leading surface 159. However, the blade 157 is truncated, so that its radially outer surface 167 is flat.

Figure 22:
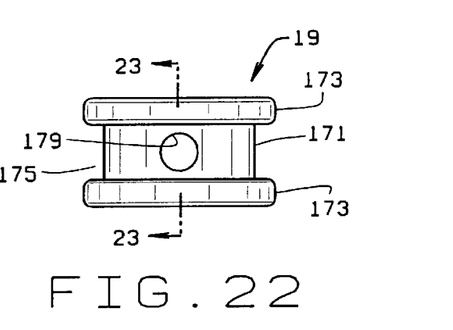
FIG. 22 is a side elevational view of a sleeve bearing used in the cartridge.
Figure 23:
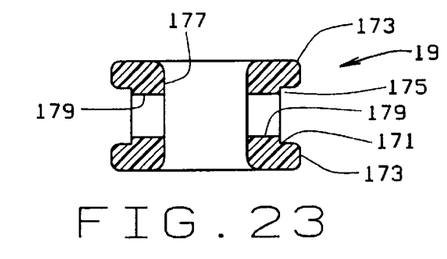
FIG. 23 is a cross-sectional view of the bearing taken along line 23—23 of FIG. 22.

The bearing 19 is shown in detail in FIGS. 22 and 23. The bearing is made from a polycarbonate, an acetal copolymer, or an acrylate. Preferably it is made from Celcon®, an acetal copolymer available from Celanese Corporation. The bearing 19 is generally bobbin shaped. It has a central circular wall 171 with top and bottom flanges 173. The flanges 173 extend beyond the wall 171 to define a channel 175. The flanges 173 have a diameter sized so that that bearings can be force fit in chambers 69b and 105. A central channel 177 extends through the bearing from the top to the bottom. The channel 177 is sized to slidingly receive the bit B. Preferably, the channel 177 is about 0.064" in diameter, which is only slightly larger than the diameter of the bit shaft. A pair of oppositely disposed ports 179 are formed in the wall 171 and communicate with the channel 177.

To assemble the cartridge, the ball bearing 21 is placed in cartridge body chamber 69d, one of the bearings 19 is placed in the chamber 69b, and the turbine 17 is placed in cartridge body 11 so that the shorter end of the turbine body 151 is received in the chamber 69a. The other bearing 19 is placed in chamber 105 in the cartridge cap 13. The cap 13 is then snapped onto the body to complete the assembly. The bit B is then placed through the cap bottom opening 111, the lower bearing 19, the turbine 17, and the upper bearing 19 until it contacts the ball bearing 21. The bearings surround the bit, rather than the turbine. The bit is frictionally received in the turbine and rotationally received in the bearings, which are generally aligned with each other. Thus, the bit defines its own axis of rotation. This substantially eliminates wobble in the bit as the bit is rotated. Additionally, the turbine body 151, the bearings 19, and the cartridge chambers 69b and 105 are sized such that the turbine will have very little room to move axially in the cartridge chamber 15. This, in connection with the ball bearing substantially eliminates bur bounce, which can be experienced with some handpieces.

In operation, water passes through cartridge body channel 73 to the bearing chamber 69b in the cartridge body head 33 to fill the bearing channel 175 with water. The water passes through the bearing ports 179 to contact the bit directly.

Water can pass along the bit B through the bearing passage 177 and enter the turbine chamber 15. The water in the turbine chamber will flow down past the turbine blades and into cap chamber 101 and the cap bearing chamber 105. In the bearing chamber 105, the water will flow through the vertical grooves 113 to enter the channel 175 of the lower bearing 19. The water will pass through the ports 179 of the lower bearing, contact the bit directly, and exit the chamber 15 through bottom opening 111 in the cap. The water also enters the interface between the turbine body 151 and the upper and lower bearings. The water at this interface helps to both cool and lubricate the turbine at these points.

Air also enters the chamber through the cartridge body passage 72 and the cartridge cap passage 137. This air is directed at the leading surfaces of the turbine blades 157 to rotate the turbine in the chamber 15, and hence to rotate the bit B. As can be appreciated, the turbine will be rotating at high speed, and the leading edges of the turbine blades and arms will contact the water droplets coming down from the upper bearing 19. Thus, the chamber 15 will be filled with a mist. This mist will also be circulating in the chamber 15. As can be appreciated, the mist has a greater mass than if only air were inside the chamber 15. This increased mass, which will be circulating in the chamber 15 will increase the momentum of the turbine, may increase the torque of the turbine. The water mist will exit the chamber 15 through the holes 115 in the cap surface 95.

Additional water passes through the cartridge passage 74 and into the cap passage 139. The cap passage 139 directs the water from passage 74 to the turbine, to help drive the turbine. Inasmuch as water has a greater mass than air, it also has greater momentum. The water can thus facilitate in driving the turbine more quickly. The water from passage 139 mixes with the air from passage 141 to form a mist which drives the turbine. The air and water in the turbine chamber 15 also exits the cartridge through the exhaust ports 115 in the floor 95 of the cap chamber 99 (also the floor of the turbine chamber 15).

As is known, water is a better heat sink than air. As described above, water will be circulating through the bearings and the chamber 15. Additionally, water will be in intimate contact with the shaft of the bit B. All this water will remove more of the heat from the cartridge during operation of the cartridge, enabling the cartridge to run more coolly. Additionally, the water also helps reduce the noise and vibration of the handpiece which occurs in air operated handpieces; and the cartridge 3 of the present invention runs very quietly.

As variations within the scope of the appended claims may be apparent to those skilled in the art, the foregoing description is set forth only for illustrative purposes and is not meant to be limiting. For example, although not shown, O-rings can be provided on the outer surface of the handle nose 6 or on the back surface of the cartridge wall 49 around the air and water ports to form fluid tight seals around the ports. Although water is passed directly to the upper bearing chamber and the turbine chamber, the head could include a further water path to direct water directly into the lower bearing chamber. These examples are merely illustrative.

We claim:

1. A high-speed medical/dental handpiece adapted to removably receive a bit; the handpiece including:

a sleeve and a head at an end of said sleeve; said sleeve carrying at least an air input tube and a water input tube, said air and water input tubes being operatively connectable to sources of air and water, said sleeve being made of an autoclavable material; and said head defining a chamber having an upper portion, a central portion, and a lower portion, said chamber lower portion having an opening therein through which the bit can pass; said chamber upper portion housing an upper bearing, said chamber central portion housing a turbine, and said chamber lower portion housing a lower bearing; said turbine being positioned between said upper and lower bearings; said air and water input tubes being in communication with said chamber to deliver operating air and water to said chamber to drive said turbine.

2. The medical/dental handpiece of claim 1 including a ball bearing in said chamber above said upper bearing; said ball bearing defining a thrust bearing for said bit.

3. The medical/dental handpiece of claim 1 wherein said air input tube is in communication with said chamber central portion and said water input tube is in communication with said chamber central portion and one of said chamber upper and lower portions.

4. The medical/dental handpiece of claim 3 wherein said upper and lower bearings and said chamber upper and lower portions cooperate to define an upper annular channel and a lower annular channel; said water input line being in fluid communication with at least one said upper and lower chamber portions to be in communication with at least one of said annular channels; said water circulating through said chamber upper portion, said chamber central portion, and said chamber lower portion.

5. The medical/dental handpiece of claim 4 wherein at least one of said upper and lower chamber portions includes an axial groove which places said at least one of said upper and lower annular channels in fluid communication with said chamber central portion.

6. The medical/dental handpiece of claim 4 wherein said upper and lower bearings each have an axial bore sized to receive the bit and a passage which places said bore in fluid communication with said annular channel, whereby water which enters said annular channels will flow through said bearing passages to contact said bit.

7. The medical/dental handpiece of claim 6 wherein the water is drawn into an interface between the bearings and the turbine.

8. The medical/dental handpiece of claim 4 wherein said chamber lower portion has a diameter smaller than a diameter of the chamber central portion; said chamber central portion having a floor; said head including exhaust passages extending through said chamber central portion floor; at least some of said air and water being exhausted through said exhaust passages.

9. The medical/dental handpiece of claim 1 wherein the bearings are plastic.

10. The medical/dental handpiece of claim 9 wherein the bearings are made of a low-temperature plastic.

11. The medical/dental handpiece of claim 10 wherein the bearings are made of a polycarbonate, an acetal copolymer, or an acrylate.

12. The medical/dental handpiece of claim 1 wherein said head of said handpiece comprises a cartridge removably receivable on an end of said sleeve; said cartridge including a body removably mountable to said sleeve and a cap mounted to said body; said body and cap cooperating to define said chamber.

13. The medical/dental handpiece of claim 12 wherein said cartridge body includes a hollow sleeve portion and a head portion; said sleeve being slidably mounted over an end of said handle; said sleeve including a snap arm having an inwardly directed finger at a free end thereof; said snap arm finger engaging said handle to hold said cartridge on said handle; said sleeve including a release arm operatively connected to said snap arm; whereby, said snap arm finger is brought out of engagement with said handle by pressing down on said release arm.

14. The medical/dental handpiece of claim 13 wherein said snap arm and release arm are both formed in a wall of said sleeve, said snap arm and release arm being pivotable about a fulcrum.

15. The medical/dental handpiece of claim 12 including a manifold at a forward end of said sleeve; said manifold including an air channel, a first water channel, and a second water channel.

16. The medical/dental handpiece of claim 15 including a groove on an inner surface of said manifold, said groove extending between said first and second water channels.

17. The medical/dental handpiece of claim 15 wherein said cartridge body includes a neck and a cartridge body head at an end of said neck; said cartridge body head including said chamber upper portion; said first water channel passing through said neck and to said cartridge body chamber.

18. The medical/dental handpiece of claim 17 wherein said cartridge cap includes a back surface which abuts a forward surface of said cartridge manifold; said cartridge cap including said chamber central portion and said chamber lower portion; said cartridge cap including an air passage in fluid communication with said cartridge air passage; said cap air passage opening into said chamber central portion.

19. The medical/dental handpiece of claim 17 wherein said cap includes a water passage in fluid communication with said cartridge second water passage; said cap water passage exiting at a lower surface of said cap to direct water at said bit.

20. The medical/dental handpiece of claim 19 wherein said cap is made of a light transmitting material; said cartridge body manifold including a light tube passage sized to accept a light tube in said sleeve; said cap including a lens in abutting relationship with said light tube passage to receive light from said light tube; said lens directing light toward said bit.

21. The medical/dental handpiece of claim 19 wherein the cartridge body includes a projection on said forward surface of said manifold; said cap including a groove sized and shaped to receive said projection; said air channel and one of said water channels passing through said projections said groove.

22. A disposable cartridge for a high-speed medical/dental handpiece adapted to removably receive a bit; the cartridge including a body and a cap defining a chamber; said chamber having an upper portion, a central portion, and a lower portion, said chamber lower portion having an opening therein through which the bit can pass; said chamber upper portion housing an upper bearing, said chamber central portion housing a turbine, and said chamber lower portion housing a lower bearing; said turbine being positioned between said upper and lower bearings; said cartridge including air and water passages positioned to direct air and water to said turbine such that said turbine is driven by air and water.

23. The cartridge of claim 22 wherein said upper and lower bearings and said chamber upper and lower portions cooperate to define an upper annular channel and a lower annular channel; said cartridge including a water passage for directing water to at least one said upper and lower chamber portions to be in communication with at least one of said annular channels.

24. The cartridge of claim 23 wherein at least one of said upper and lower chamber portions include axial grooves which place at least one of said upper and lower annular channels in fluid communication with said chamber central portion.

25. The cartridge of claim 23 wherein said upper and lower bearings each have an axial bore sized to receive the bit and a passage which places said bore in fluid communication with said annular channel.

26. The cartridge of claim 22 including a floor and at least one exhaust port in said floor for exhausting air and water from said chamber; said exhaust port being separate from said opening for the bit.

27. The cartridge of claim 26 including a plurality of exhaust ports arranged in an arc adjacent a wall of said cartridge.

* * * * *